United States Patent [19]

Yaroshuk et al.

[11] 4,219,277
[45] Aug. 26, 1980

[54] METHOD OF DETECTING FLAWS ON SURFACES

[75] Inventors: Nick Yaroshuk, White Oak; Miklos Sarkozi; Eugene G. Vaerewyck, both of Murrysville, all of Pa.

[73] Assignee: Westinghouse Electric Corp., Pittsburgh, Pa.

[21] Appl. No.: 932,234

[22] Filed: Aug. 9, 1978

[51] Int. Cl.² ............................................. G01N 21/22
[52] U.S. Cl. .................................. 356/431; 356/237; 250/563
[58] Field of Search ................. 356/51, 237, 430, 431, 356/445; 250/563, 572

[56] References Cited

U.S. PATENT DOCUMENTS

| | | | |
|---|---|---|---|
| 2,975,293 | 3/1961 | Kruse, Jr. et al. | 250/219 |
| 3,749,496 | 7/1973 | Hietanen et al. | 356/73 |
| 3,781,117 | 12/1973 | Laycak et al. | 356/200 |
| 3,781,531 | 12/1973 | Baker | 235/151.3 |
| 3,804,534 | 4/1974 | Clarke | 356/237 |
| 3,812,373 | 5/1974 | Hosoe et al. | 250/562 |
| 3,834,822 | 9/1974 | Stapleton et al. | 356/431 |
| 3,843,890 | 10/1974 | Anthony, Jr. et al. | 250/563 |
| 3,900,265 | 8/1975 | Mevlen et al. | 356/200 |
| 3,920,970 | 11/1975 | Slaker | 235/151.3 |
| 3,984,189 | 10/1976 | Seki et al. | 356/73 |

*Primary Examiner*—John K. Corbin
*Attorney, Agent, or Firm*—R. A. Stoltz

[57] ABSTRACT

This invention is an improved method for scanning for flaws on a surface utilizing dynamic correction. Each individual scan signal is divided into a large number of increments, each increment representing a predetermined position in the scan. A dynamic average is computed for each of the scan positions and flaws are detected by comparing the increment signals to the dynamic average signal for the same position. This technique is especially useful to detect flaws on high quality tubing, such as used for nuclear reactor fuel rods or for nuclear reactor steam generator tubing.

6 Claims, 3 Drawing Figures

METHOD OF DETECTING FLAWS ON SURFACES

CROSS-REFERENCE TO RELATED APPLICATION

In concurrently filed application Ser. No. 932,235, assigned to the same assignee, is described a system for automatically classifying defects, both for sorting defective tubing as to the operations required for correcting the defect and for classifying the defect as to the probable preceding operation which caused that defect and sending a signal to that operation.

BACKGROUND OF THE INVENTION

This invention relates to a technique for detecting flaws on surfaces, and, more particularly, to automatically and dynamically correcting for variations in signals from position-to-position as well as drift of various parameters with time.

Before the development of this technique, tubing inspection on nuclear reactor steam generator tubing and the Zircaloy nuclear reactor fuel rods was performed manually. Such visual flaw/defect inspection tasks are dependent upon human operation and interpretation. This method lacks a definitive and accurate reference, lacks consistency, is slow and tedious, and adds significantly to product cost. Where ultra-high reliability is required, however, none of the prior art automatic scanning systems were able to locate defects as effectively as the human inspectors.

A large number of surface scanning systems have been proposed in the past. U.S. Pat. No. 2,975,293 issued to Kruse et al. on Mar. 14, 1961 and U.S. Pat. No. 3,804,534, issued to Clarke on Apr. 16, 1974 illustrate such scanning systems. The use of more than one detector for rough surfaces is taught, for example, in U.S. Pat. No. 3,984,189 issued to Seki et al. Generally, the prior art scanning systems were designed for flat surfaces, but U.S. Pat. No. 3,749,496 issued to Hietanen et al. on July 31, 1973 illustrates the inspection of the inside surface of a cylindrical workpiece. Generally the inspection device is stationary and the surface is moved past it.

Some systems have used electronic logic or memories for defect evaluation including means to prevent indications of multiple flaws when a single flaw is scanned by consecutive scans. See, for example, the following U.S. Pat.: Nos. 3,900,265 issued to Merlen et al. on Aug. 19, 1975; 3,812,373 issued to Hosoe et al. on May 21, 1974; and No. 3,781,117 issued to Laycak et al. on Dec. 25, 1973. Some systems use averaging of the signal from the preceding portion of the scan (passing the scan signal through a low pass filter) to develop a base line signal, and then compare the instantaneous signal to the base line signal in order to partially compensate for the gradual variations in sensitivity throughout a scan. U.S. Pat. Nos. 3,781,531 issued to Baker on Dec. 25, 1973 and 3,920,970 issued to Slaker on Nov. 18, 1975 illustrate this technique. The sensitivity of such circuits is limited as the error threshold must be set away from the base line not only by the normal amount of noise, but also by the amount which the base line shifts during the filtering period.

While the prior art methods have been satisfactory for some applications, higher quality products, such as nuclear reactor fuel tubing and nuclear reactor steam generator tubing have required closer inspection than what was provided by the prior art automatic scanning systems. As a result, slow manual inspection methods have been heretofore used for such products.

SUMMARY OF THE INVENTION

This invention provides a extremely sensitive method for scanning for flaws on a surface. It uses separate dynamic averages for each of the many increments into which the scan has been divided and then, on an increment-by-increment basis compares the latest value of each increment to the average value for increments in that position in the scan. In this manner, each position within the scan is dynamically corrected both for variations in sensitivity with position in the scan as well as such non-position related variations as long term drift in the source of electromagnetic radiation or in the radiation sensor or in the electronic circuitry.

The surface is generally moved past the scanner perpendicular to the direction of scanning and the scan is repeated to produce a number of scan signals. Each scan signal is divided into a large number of (generally at least 100) scan increments with each scan increment being identified as to its position within the scan by its time relationship within the serial scan. Each of the signal increments are combined with the corresponding position increments from earlier scans to provide a large number (again generally at least 100) of dynamic average signals. Each of the latest signal increments are then compared to the corresponding dynamic average signal to generate a signal indicative of surface condition for that scan position.

This invention is especially useful when very high quality product is required (e.g., for applications such as nuclear fuel tubes and tubing for nuclear steam generators).

BRIEF DESCRIPTION OF THE DRAWINGS

A better understanding of the invention may be had by reference to the drawings, in which.

DESCRIPTION OF THE PREFERRED EMBODIMENTS

Figure 1:
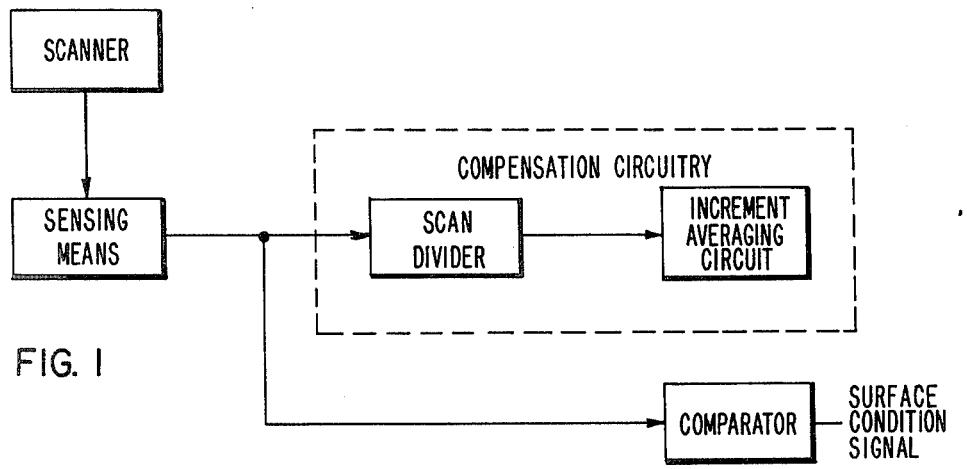
FIG. 1 is a block diagram showing the relationship between key elements of the invention.

The scanner and sensing means of FIG. 1 can be any of a variety of configurations which provide a serial signal with time (not parallel signals from different positions) of the type given by a sensor repeatedly moved across a surface. The scanning can be provided by moving the spot of radiation directed onto the surface to be inspected, or providing a source of radiation covering the entire line to be scanned and moving the sensor of the reflected radiation, or by having a constant line of radiation impinging on the surface and having a large number of sensors and electronically scanning the sensors to produce a serial output signal substantially the same as the other techniques. In any case the amplitude of the serial output signal is to be a function of the radiation reflected from the surface, and the timing within the scan is to be related to position within the scan. At any one point in time, the signal (or signals) represent reflection from a single small spot on the surface.

While a surface could be scanned by parallel channels (by reflecting a relatively long thin line of light off the surface and using a large number of stationary sensors and continuously monitor all sensors in parallel) such a parallel configuration requires a large amount of electronics and is quite expensive. It also requires a large number of wires with a large number of connections and thus is much less reliable. Such a parallel configuration does not produce a serial signal and is not within the scope of this invention.

The preferred embodiment of this invention is with a stationary laser whose beam is passed through an acoustical scanner to cause the laser beam to be repeatedly scanned across the surface. The sensors are also stationary and the surface is moved past the system such that the line scanned by the laser beam will inspect the surface area. Although a single sensor could be used, three sensors are preferred to provide better identification of the type of defect. The system is adjusted so that most of the energy is reflected to the center sensor system (when the spot on the surface being scanned is defect-free). Defects such as dents or scratches will deflect more light to an outside sensor while other defects (such as stains or pits) will lower the radiation received by the center channel without increasing the radiation received by either of the outside sensors. Defect analysis is dealt with in more detail in the aforementioned concurrently filed application.

This invention is basically a single system for compensating for multiple types of variations (long-term and short-term, position related and non-position related within the system. Rather than individually compensating for several variables (measuring the laser output and feeding back this signal to maintain a constant laser output with time, with another system for measuring the variations in the acoustical scanner as a function of angle and having a separate system to correct for variations, and putting in another separate correction system for variations with position in the sensors) all corrections are made by a single system of compensation circuitry.

The compensation circuitry produces dynamic averages on an increment (small scan segment) by increment basis. Thus, if a particular increment of the scan remains low, scan after scan, because of a nonlinearity in the optical scanner for example, the dynamic average in that portion of the scan will be low and will compensate for the nonlinearity.

Vibration can be especially troublesome during inspection of tubing. Dynamic averaging compensates for vibration if the averaging is done over a comparatively short period. Averaging over about 16 scans with 5300 scans per second has proven satisfactory for tube inspection.

Figure 2:
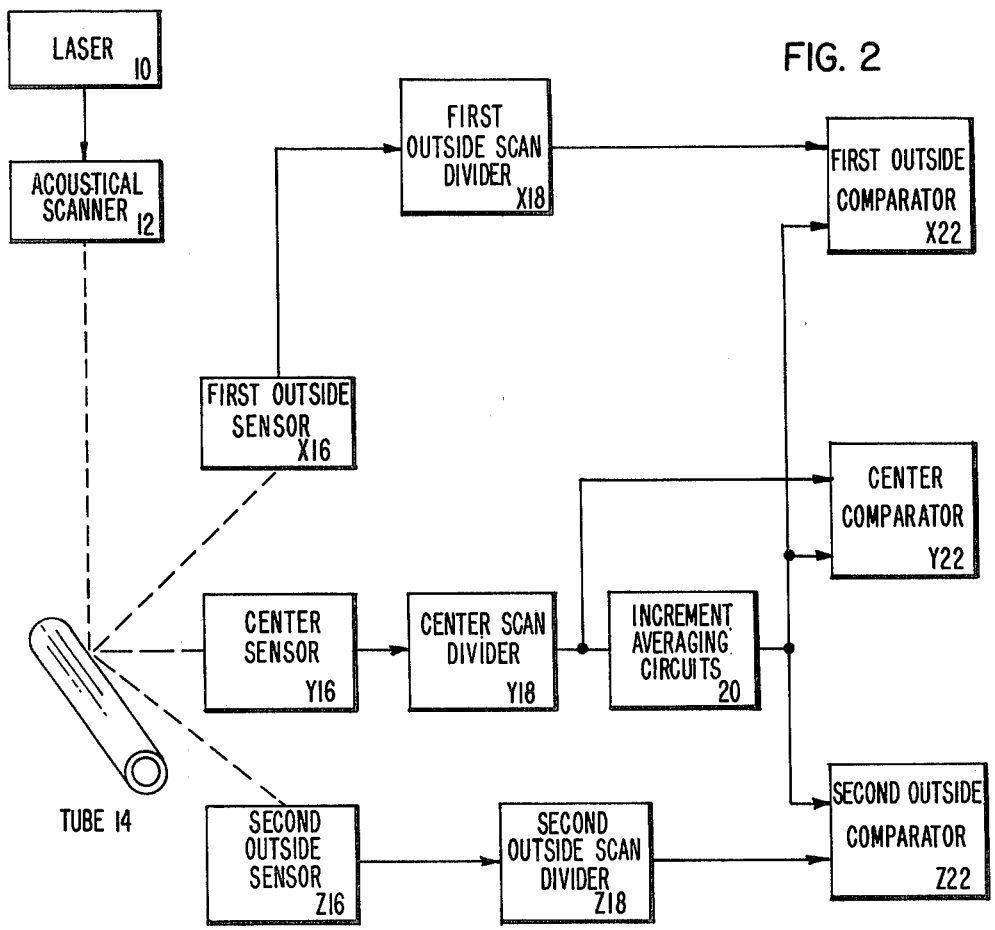
FIG. 2 is a block diagram showing a three sensor arrangement.

The block diagram in FIG. 2 shows a three-sensor arrangement in which the dynamic average of the center sensor is used as a basis for comparison for all three sensor signals. In this configuration a laser beam is repeatedly scanned across the surface of the tube by an acoustical scanner. The tube is simultaneously fed axially and rotated such that the scanning lines cover the entire surface of the tube (during one rotation the tube is fed axially just less than the length of the scan so that there is a small amount of overlap). The system is adjusted (with no defect on the tube) so that most of the light is reflected to the center sensor but with a detectable amount of light in each of the outside sensors. Some types of defects, such as dents, may cause a reduction in the amount of light reaching the center sensor (the "Y" sensor) but an increase in the amount reaching one of the outside sensors (the "X" or "Z" sensors). Other types of defects, such as pits or stains, will cause a reduction in the amount of light reaching the center sensor but will not increase the light received in either of the outside sensors. In this particular system each scan is divided into 128 increments and a dynamic average value is computed for each one of these 128 increments. Thus, at the time the laser beam is in a position approximately half way through the scan (on the 64th increment, for example) three 64th increment values will be sensed (one for each of the outside channels and one for the center channel). All three of these 64th increment values will be compared to the average value (of the center sensor) for the 64th increment in past scans.

Figure 3:
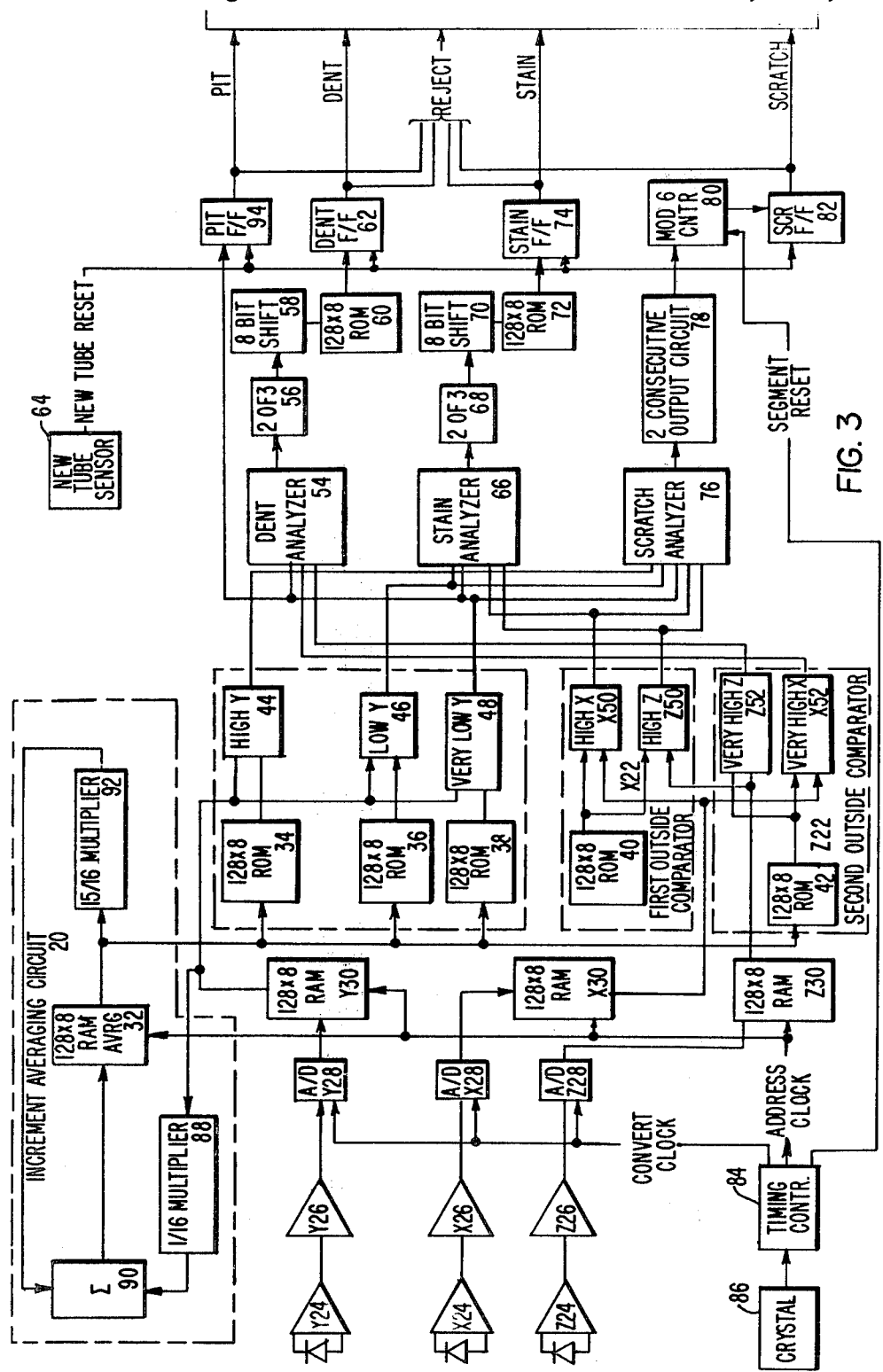
FIG. 3 is a diagram showing details of the surface analysis circuitry.

FIG. 3 shows details of a particular embodiment. In this embodiment the serial analog signal from the three sensors (here silicon photodiodes) are run through amplifiers to A-to-D converters to produce 128 digital values per sensor per scan. These three sets of 128 digital values are stored in order in three random access memories. In this embodiment, there is a scan portion of the cycle, during which the laser beam scans the tube and the sensor values are digitized and stored, and also an analyzing portion of the cycle (here using the same length of time as the scan portion) in which the data in each position in the X, Y and Z random access memories ($X_i$, $Y_i$ and $Z_i$) is compared to the average value in the Y channel for that position in the scan. When the comparison of any increment of the X, Y and Z signals falls outside certain predetermined limits, an error signal is generated (in most cases, multiple error indications are necessary to cause a reject).

In particular, light (from a laser, scanned by an acoustic scanner, and reflected off the tube surface as in FIG. 2) is picked up by silicon photo diodes X16, Y16 and Z16. Referring to FIG. 3, the electrical signal is amplified by X24, Y24, Z24 and further amplified by X26, Y26, and Z26. During the scan portion of the cycle, the convert clock pulse causes each of the A-to-D converters X28, Y28 and Z28 to generate 128, 8-bit incremental signals (each of the incremental values being represented by 8 binary bits). These incremental signals are then stored in order by position within the scan in 128 by 8 random access memories X30, Y30 and Z30. After the scan portion is complete, the analyze portion begins and the address clock addresses the first memory position (the first scan increment) in the random access memories X30, Y30 and Z30 and also the first position in the increment average random access memory 32. The average value for this first increment is then multiplied by predetermined constants using read only memories 34, 36, 38, 40 and 42 (here, read only memories are used in a table lookup fashion to provide multiplication by the predetermined constant) to provide several threshold values for comparison. The latest values for X, Y and Z for the first incremental position ($X_i$, $Y_i$, and $Z_i$) are compared to the threshold values in comparators 44, 46, 48, 50, 52, 54 and 56 to provide indication of when the X, Y, or Z signal has deviated from its normal relationship to the center sensor average for that first increment. Thus, for example multiplier 34 gives an effective multiplication of about 1.2 and comparator 44 will provide an output when the latest value of Y exceeds 1.2 times the corresponding increment average of Y. Similarly, multiplier 36 provides a constant such that comparator 46 gives an output when the Y value ($Y_i$) is less than 60 percent of $\overline{Y}_i$ ($\overline{Y}_i$ being the average value of Y for that increment). Similarly, multiplier 38 and comparator 48 given output on a very low values of Y (when $Y_i$ is less than 0.5 times $\overline{Y}_i$). Multiplier 40 and comparators X50 and Z50 provide an output when the latest X or Z values ($X_i$ or $Z_i$) rise above about 45 percent of $\overline{Y}_i$. Multiplier 42 and comparators X52 and Z52 provide outputs when either $X_i$ or $Z_i$ rise above 60 percent of $\overline{Y}_i$.

As discussed in the above-mentioned concurrently filed application, the logic circuitry not only indicates rejects, but also classifies the defects. This allows for sorting the tubes for subsequent analysis and repair, and also for signalling the appropriate preceding work stations such that process alterations may be made which will minimize the number of defects. Generally, the defects are classified as "pits", "dents", "stains", or "scratches". "Dent" analyzer 54 is activated by a very low $Y_i$ ($Y_i^{--}$) from comparator 48, together with a high $X_i(X_i^+)$ or $Z_i(Z_i^+)$ from comparators Z52 or X52. Two error indications out of three consecutive increments will provide an output from the dent two-out-of-three circuit 56. Filtering circuits such as circuit 56 provide smoothing to minimize erroneous error signals (e.g., those generated by electrical noise). The output from the two-out-of-three circuit 56 is further filtered by an 8-bit shift register 58 and by the pattern analysis circuit 60 (here a 128×1 read only memory). This arrangement of shift register plus read only memory is currently being used to indicate two consecutive outputs of the two-out-of-three circuit 56. When the "dent" criteria is met, the "dent" flip-flop 62 is set, the tube is marked for rejection. The "dent" rejection signal is maintained until reset by the new tube sensor 64. The "dent" analyzer circuit 54 is activated by the $Y_i$ very low signal from comparator 48 simultaneously with either the $X_i$ or $Z_i$ very high signal from comparators X52 or Z52.

The "stain" analyzer 66 includes a two-out-of-three circuit 68, shift register 70, read only memory 72, and stain flip-flop 74 and operates in a similar manner to the previously described dent circuit except that the criteria for an output of the "stain" analyzer 66 is a $Y_i$ low ($Y_i^-$) indication from comparator 46, but not a very low $Y_i$ ($Y_i^{--}$) indication from comparator 48 and also neither a high $X_i$ nor high $Z_i$ indication from comparators X50 or Z50. Thus, the control equation is: $Y_i^-$ and not $Y_i^{--}$ and not ($X_i^+$ or $Z_i^+$).

The "scratch" analyzer circuit gives an output with low $Y_i$ from comparator 46 but not very low $Y_i$ from comparator 48. High $X_i$ from comparator X50 or high $Z_i$ from comparator Z50 but not high $Y_i$ from comparator 44 is also interpreted as a "scratch". Thus, the control equation is: ($Y_i^-$ and not $Y_i^{--}$) or (($X_i^+$ or $Z_i^+$) and not $Y_i^+$). The output of analyzer 76 goes into a filtering arrangement consisting first of the two-consecutive-output circuit 78 and then the counter 80. Counter 80 is reset by the segment reset every 32 scans. If the counter 80 gets to 6 before being reset, it sets the "scratch" flip-flop 82 and marks the tube to be rejected.

The segment reset, like the convert clock (during the scan portion of the cycle) and the address clock (during the analyze portion of the cycle) is generated by the timing and control circuit 84 which, in turn, is driven by the 20 MHz crystal oscillator 86.

The average for each increment of the scan ($\overline{Y}_i$) is calculated during the analysis cycle at the same time the $X_i$, $Y_i$, and $Z_i$ values are analyzed. As each increment is addressed by the address clock, the output of the random access memory Y30 is fed through a times 1/16 multiplier 88 and then to a summing circuit 90. The $\overline{Y}_i$ calculated on the previous cycle is fed from the averaging random access memory 32 through a times 15/16 multiplier 92 (at the same time, the $\overline{Y}_i$ value is also being fed to multipliers 34, 36, 38, 40 and 42 for comparison to $X_i$, $Y_i$ and $Z_i$). The output of the 15/16 multiplier 92 is fed to the summing circuit 90 where it is combined with the output of multiplier 88 (1/16 the latest value of $Y_i$) and this updated value of $\overline{Y}_i$ is then stored back in the averaging random access memory 32. This process is repeated to calculate a new $\overline{Y}_i$ value for each of the 128 increments during each analysis period.

The analysis circuit for "dents", "stains" and "scratches", as described above, uses special or shift register and read only memory combinations 58 and 60, 70 and 72 to provide filtering to avoid rejection from electrical noise or on minor surface blemishes. The "pit" detection circuitry, however, has no such filtering as even a very small pit could represent a serious defect. The Y very low ($Y_i^{--}$) indication from comparator 48 is an indicator of a pit and this output is fed directly to the "pit" flip-flop 94. Thus, a single incident of output from the $Y_i^{--}$ comparator 48 will cause rejection of the tube.

Although the arrangement described above has been found to be very practical and effective, many of the circuit details are, of course, arbitrary and the function of the invention can be provided in other ways. Clearly the criteria for what is considered to be a "dent", "stain" or "scratch" are somewhat arbitrary and could easily be altered. Similarly, other types of multipliers (other than the read only memories 34, 36, 38, 40 and 42) can be used and their threshold values (their multiplication constants) could be varied. Likewise, there are other arrangements which could be used for the increment averaging circuit 20 to produce increment-by-increment $\overline{Y}$ values (e.g. the 15/16 weighting for the old average and 1/16 weighting for the most recent value is convenient, but not critical). Other types of averaging could also be used, such as combining $Y_i$ from the previous scan with $Y_i$ from the scan which preceded that (with, for example, ½ weighting each) as could be accomplished by two 128 by 8 memories being updated with the latest $Y_i$ on alternate cycles.

Similarly it is convenient, but not critical to use a separate cycle portion for scan and analysis. In fact, data from a number of scans could be recorded and analyzed by a separate piece of equipment at some later time. While a greater number of increments than 128 could be used, this number preferably should not be substantially reduced (i.e., to less than 100) as either the speed or the resolution (especially for small pits) obtainable by this method will be seriously reduced. In no case, should less than 30 increments be used.

As additional variations can be made without varying the inventive concept described herein, the invention should not be construed as limited to the particular forms described, and these described forms are to be regarded as illustrative rather than restrictive. The invention is intended to cover all forms which do not depart from the spirit and scope of the invention.

We claim:
1. In a method of surface measurement of the type which utilizes advancing a surface past a source of electromagnetic radiation directing said electromagnetic radiation toward said surface, sensing radiation reflected from said surface with an electromagnetic radiation sensing means, effectively scanning at least one of said source and said radiation sensing means repeatedly through identifiable positions across said surface generally perpendicular to the direction in which said surface is advanced, to produce a series of serial scan signals, the improvement comprising:

a. dividing each of said scan signals from at least two of said series of scans into at least 30 signal increments, each signal increment being identifiable as to position in the scan;

b. combining signal increments from the same position of at least one other scan signal to produce at least 30 position related dynamic average signals;

c. dividing a scan signal from an additional scan into at least 30 additional positions related signal increments; and d. comparing said additional increment signals with the dynamic average signal for the same position to generate a signal indicative of surface condition.

2. The method of claim 1, wherein said surface is an outer tube surface and said tube surface is simultaneously rotated and fed axially past a scanning light beam and at least one stationary detector.

3. The method of claim 2, wherein at least two stationary detectors are used to monitor reflections from said surface.

4. The method of claim 3, wherein said source of electromagnetic radiation is a laser which generates a laser beam and wherein an acoustical scanner is used to scan the beam from said laser.

5. The method of claim 4, wherein said tubes are tubes for nuclear fuel elements.

6. The method of claim 5, wherein said scan signal is divided into at least 100 increments.

* * * * *